(12) United States Patent
Arnold, Jr. et al.

(10) Patent No.: US 7,169,361 B2
(45) Date of Patent: Jan. 30, 2007

(54) PIPETTE TIP RELOADING SYSTEM

(75) Inventors: Robert W. Arnold, Jr., La Mesa, CA (US); Christian Deschenes, Atlanta, GA (US); Douglas R. Boyer, San Diego, CA (US)

(73) Assignee: Molecular BioProducts, Inc., San Diego, CA (US)

( * ) Notice: Subject to any disclaimer, the term of this patent is extended or adjusted under 35 U.S.C. 154(b) by 295 days.

(21) Appl. No.: 10/044,824

(22) Filed: Jan. 10, 2002

(65) Prior Publication Data
US 2003/0129089 A1 Jul. 10, 2003

(51) Int. Cl.
B01L 3/02 (2006.01)
B65D 1/34 (2006.01)
B65D 6/04 (2006.01)

(52) U.S. Cl. ............... 422/100; 99/104; 99/931; 206/562; 206/563; 206/821

(58) Field of Classification Search ......... 422/99–100, 422/104, 931; 206/142, 199, 562–563, 821
See application file for complete search history.

(56) References Cited

U.S. PATENT DOCUMENTS

| | | | |
|---|---|---|---|
| 4,577,760 A | 3/1986 | Rainin et al. | |
| 4,651,873 A * | 3/1987 | Stolcenberg et al. | 206/142 |
| 5,232,669 A * | 8/1993 | Pardinas | 422/100 |
| 5,324,482 A | 6/1994 | Scaramella et al. | |
| 5,392,914 A * | 2/1995 | Lemieux et al. | 206/499 |
| 5,441,702 A * | 8/1995 | Lemieux et al. | 422/100 |
| 5,470,538 A | 11/1995 | Lind | |
| 5,612,000 A * | 3/1997 | Lemieux | 422/100 |
| 5,622,676 A | 4/1997 | Lind | |
| 5,630,988 A | 5/1997 | Stolp | |
| 5,642,816 A | 7/1997 | Kelly et al. | |
| 5,735,562 A * | 4/1998 | Borg | 294/87.2 |
| 5,779,984 A | 7/1998 | Kelly et al. | |
| 5,827,745 A | 10/1998 | Astle | |
| 5,882,603 A | 3/1999 | Taggart | |
| 5,948,362 A * | 9/1999 | Steinbrenner et al. | 422/100 |
| 6,007,779 A * | 12/1999 | Lemieux et al. | 422/100 |
| 6,059,099 A * | 5/2000 | Galbierz | 206/151 |
| 6,098,802 A | 8/2000 | Asa et al. | |
| 6,164,449 A * | 12/2000 | Lahti | 206/499 |
| 6,182,719 B1 | 2/2001 | Yahiro | |
| 6,221,317 B1 | 4/2001 | Carl | |
| 6,286,678 B1 * | 9/2001 | Petrek | 206/443 |
| 6,514,466 B2 * | 2/2003 | Labriola et al. | 422/104 |
| 6,534,015 B1 * | 3/2003 | Viot et al. | 422/102 |

(Continued)

FOREIGN PATENT DOCUMENTS

DE 44 19 291 6/1994

(Continued)

*Primary Examiner*—Brian R. Gordon
(74) *Attorney, Agent, or Firm*—Andrus, Sceales, Starke & Sawall, LLP

(57) ABSTRACT

A pipette tip reloading system permits the reuse of a tip holder in a manner which interposes no additional transfer structure between the tip holder and the replacement tips. The reloading system includes a tip transfer tray and a push plate which releases the tips from the tray in a simple and reliable manner. The push plate also helps maintain alignment of the tips on the transfer tray as they are moved into position on the tip holder.

11 Claims, 5 Drawing Sheets

U.S. PATENT DOCUMENTS 7,060,226 B1 * 6/2006 Jessop et al. ............... 422/100
2003/0152494 A1 * 8/2003 Moritz et al. ............... 422/104

FOREIGN PATENT DOCUMENTS

| | | |
|---|---|---|
| DE | 694 09 629 | 3/1995 |
| EP | 0 985 451 | 3/2000 |
| WO | WO 02/072261 | 9/2002 |
| WO | 03/043739 A1 | 5/2003 |

* cited by examiner

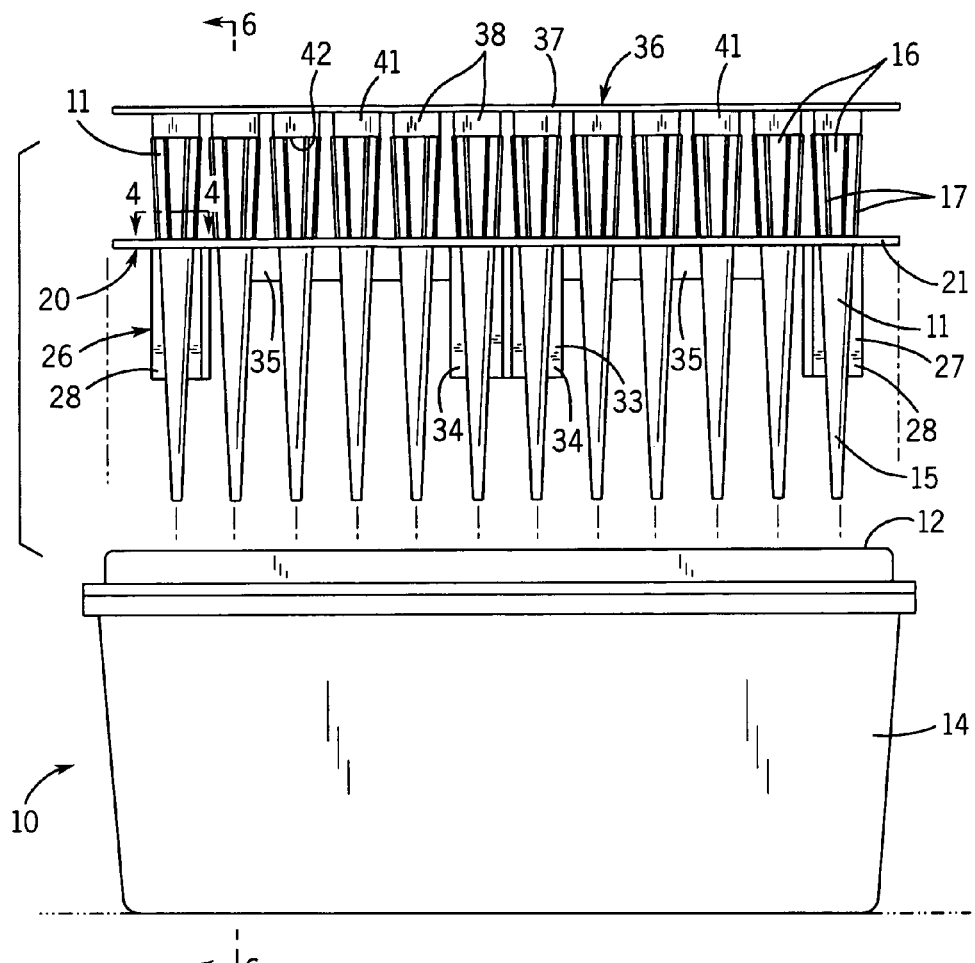
FIG. 3
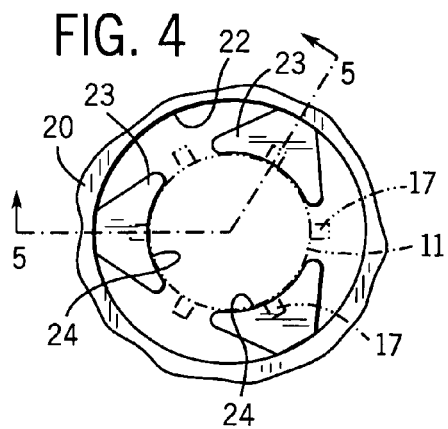
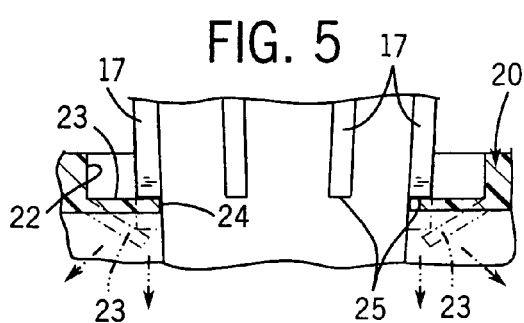

PIPETTE TIP RELOADING SYSTEM

BACKGROUND OF THE INVENTION

The present invention pertains to a method and related apparatus for reloading a conventional pipette tip holder with an array of replacement pipette tips and, more particularly, to a system in which the replacement pipette tips are loaded into the holder without interposing any transfer device between the holder and the tips.

In biochemical, pharmaceutical and clinic testing, pipetting apparatus is used to transfer small volumes of reagents and samples for various types of testing and assay procedures. Pipette tips are conventionally furnished in tip holders which carry 96 pipette tips in a rectilinear 8×12 array. The tip holder includes a flat support surface provided with an array of openings for the pipette tips which are supported fairly loosely therein so they may be easily picked up with the probe tip of a pipettor device. Furthermore, pipettors may be adapted to pick up a single tip or multiple tips at one time, typically multiple tip pipettors will pick up eight or twelve tips (comprising an entire row in a tip holder) at one time.

A pipette tip holder also typically comprises an enclosing box having a removable cover. The flat tip support surface carrying an array of tips generally lies over the top of the box with the lower tapered tip ends extending downwardly into the box and the upper ends of the tips, comprising mounting collars for receipt of the pipettor probes, extending upwardly from the support surface and enclosed by the lid. It has long been recognized that there are economies in reloading a pipette holder with replacement tips once it has been emptied, instead of discarding the entire tip holder box. It has also been long recognized that reloading an empty pipette tip holder required apparatus and methods that would permit the transfer of an entire array of 96 tips in order to make reloading practical. The reloading apparatus is usually less expensive than the original tip holder, but it should also be simple to use, be capable of packaging to facilitate shipment and storage, and minimize the amount of scrap.

A number of prior art reloading systems have been developed with the intent of addressing the foregoing requirements. Several of these systems utilize a simple carrier or transfer plate in which an array of 96 pipette tips is carried to and placed on the support surface of an empty tip holder, whereafter the pipettor may connect to and withdraw a tip or tips in the usual way. However, such prior art tip transfer devices are either unduly complex or do not provide sufficient stability and alignment for the replacement array of tips so that they may be easily inserted into the openings in the original pipette holder without undue adjustment and maneuvering. Furthermore, because conventional pipette tip holders are often utilized with mechanical or robotic pipettor devices that are adjusted or programmed to move to and from fixed pipette tip locations, reloading systems which place a transfer plate or card filled with replacement tips onto the pipette holder change the locations of the upper ends of the pipette tips (progressively raising the positions with each replacement array), so that they may interfere with the operation of a mechanical or robotic pipettor.

The subject invention addresses all of the requirements of a pipette tip replacement or reloading system but, in addition, does so without placing and leaving any transfer plate or other device on the tip holder between the holder support surface and the replacement pipette tips.

SUMMARY OF THE INVENTION

The apparatus of the present invention comprises a system for placing an array of pipette tips in an empty pipette holder, the pipette tips each typically having a lower tapered tip end and an upper mounting sleeve, and the pipette holder having a generally flat support surface which is provided with an array of openings that are adapted to receive and hold the array of tips in a tip support position, the system further comprising a transfer tray that has an array of apertures arranged to align with the array of openings in the pipette holder, each of the apertures in the transfer tray having a peripheral edge portion that is adapted to and hold a pipette tip by its mounting sleeve with the tip extending downwardly from the underside of the transfer tray; and, a push plate that is adapted to overlie the transfer tray and to engage the mounting sleeves of the tips and push the same through the apertures in the transfer tray and into the tip support position on the pipette holder. Preferably, the transfer tray has a flat upper surface, and the apertures in the tray are sized to support the pipette tip mounting sleeves at their lower edges.

In a preferred embodiment, the transfer tray has a main body portion of generally uniform thickness, the apertures are formed in said main body portion, and the peripheral edge portions of the apertures are formed from a plurality of flexible lips that extend radially inwardly from the edges of the apertures. Preferably, the flexible lips are substantially thinner than the thickness of the main body portion. The main body portion of the transfer tray has a generally flat underside and the flexible lips are generally coplanar with the flat underside. In one embodiment, there are three flexible lips for each aperture, the lips positioned equally spaced around the aperture periphery.

The underside of the transfer tray is provided with a support structure that depends downwardly therefrom and is engageable with the flat support surface of the pipette tip holder to hold the tips above the support position with the tip ends extending into the pipette holder openings. The support structure preferably comprises a plurality of legs that extend generally perpendicular to the transfer tray and are positioned between adjacent apertures.

The push plate may comprise an upper body that has a generally planar undersurface and an array of fingers extending downwardly from the undersurface and arranged to align with and extend into the mounting sleeves of the tips in the transfer tray. Each of the downwardly depending fingers on the push plate includes a tapered distal end that is sized to extend into the mounting sleeve of a tip, and a generally cylindrical proximal end that is sized to pass through a transfer tray aperture and which forms at its juncture with the distal end a shoulder that is adapted to engage the upper edge of the pipette tip mounting sleeve.

The method of the present invention relates to reloading a pipette tip holder of the type having a generally flat support surface that is provided with an array of openings adapted to receive and hold an array of tips in a tip support position with the tip ends pointing downwardly, the method comprising the steps of (1) supporting the array of tips in an array of apertures on a transfer device, the apertures arranged to align with the array of openings in the pipette tip holder, (2) positioning the transfer device and the array of tips supported thereon over the holder with the tip ends extending into the openings, and (3) pushing the tips downwardly through the transfer device and into the tip support position on the tip holder. The pipette tips are typically of the type having a tapered tip end and an upper mounting sleeve defining a shoulder with the tip end and, in accordance with the preferred method of the present invention, the supporting step comprising engaging the shoulders of the mounting sleeves of the tips in the peripheries of the apertures in the transfer device. Preferably, the peripheries of the apertures in the transfer device are defined by resilient flexible lips, and the supporting step comprises resiliently supporting said tip mounting sleeves with said lips.

The transfer device includes a generally flat upper body that contains the apertures and a support structure that depends downwardly from the body, and the positioning step comprises engaging the flat support surface of the holder with said support structure. In accordance with the presently preferred embodiment of the method, the pushing step comprises the steps of (1) placing a push plate on top of the tip mounting sleeves in the transfer device, and (2) pushing the push plate downwardly to simultaneously push all of the tips through the transfer device. Preferably, the step of placing the push plate on top of the tip mounting sleeves in the transfer device is performed prior to the positioning step.

In a variant method for reloading an empty pipette tip holder with an array of pipette tips, the pipette tips each having a lower tapered end and an upper mounting sleeve, and the pipette tip holder having a generally flat support surface provided with an array of openings adapted to receive and loosely hold the array of tips in a tip support position, the method comprises the steps of (1) providing a transfer tray having a generally flat body with an array of apertures arranged to align with the array of openings in the holder, (2) forming each of the apertures with a flexible peripheral edge portion that is sized to hold a pipette tip by its mounting sleeve with the tip extending downwardly from the underside of the transfer tray body, (3) engaging the mounting sleeves of the tips with a push plate having a plurality of downwardly depending protrusions corresponding to and alignable with the pipette tips in the transfer tray, and (4) pushing the tips through the apertures and past the edge portions into the tip support position on the pipette holder. The method also preferably comprises, prior to the pushing step, the step of holding the pipette tips above the support position with the support structure depending downwardly from the underside of the transfer tray and in engagement with the flat support surface of the pipette holder. The holding step preferably comprises supporting the pipette tips in the transfer tray with the tip ends extending downwardly past the support structure.

BRIEF DESCRIPTION OF THE DRAWINGS

FIG. 2a is an enlarged detail taken on line 2a—2a of FIG. 2.

FIG. 3 is a side elevation view of the components of the pipette tip reloading system of the present invention in association with a conventional tip holder.

FIG. 4 is an enlarged sectional detail taken on line 4—4 of FIG. 3.

FIG. 5 is a sectional detail taken on line 5—5 of FIG. 4.

DETAILED DESCRIPTION OF THE PREFERRED EMBODIMENT

Figure 1:
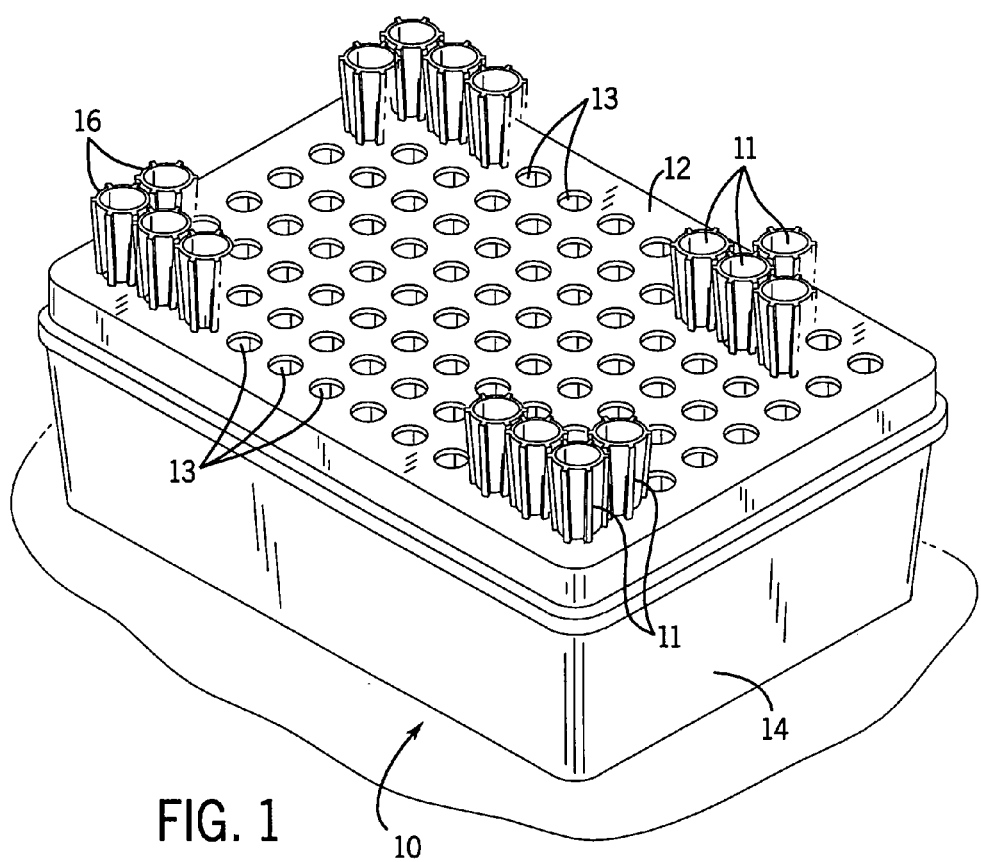
FIG. 1 is an isometric view of a conventional pipette tip holder showing a portion of an array of pipette tips held thereon.

FIG. 1 shows a pipette tip holder 10 of a type typically used to support an array of 96 pipette tips 11 arranged in the holder in eight rows of 12 tips each. The tip holder 10 includes a flat support surface 12 which is provided with the rectilinear 8×12 array of openings 13 into which the pipette tips 11 are inserted and loosely held for subsequent attachment to and withdrawal by a pipettor (not shown). The support surface 12 is mounted on the upper edge of a generally rectangular container 14. An enclosing lid, not shown, is placed over the support surface and container to enclose the pipette tips 11 for shipping and storage, all in a manner well known in the art.

Figures 7, 8:
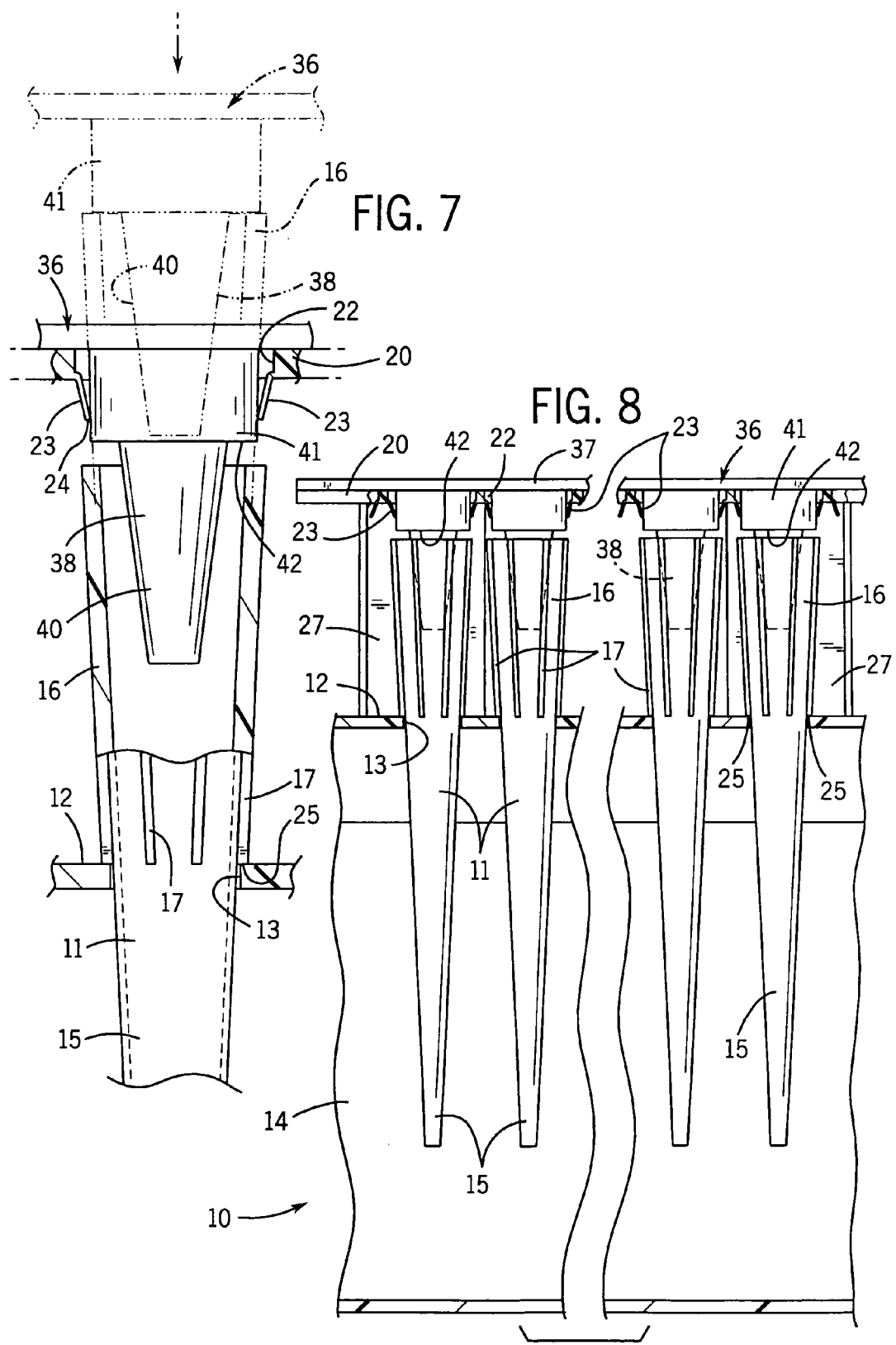
FIG. 7 is an enlarged sectional detail showing the transfer sequence of a pipette tip from the transfer tray to the tip holder.
FIG. 8 is an elevation view similar to FIG. 6 after transfer of the tips to the tip holder has been effected.

Referring also to FIG. 8, the pipette tips 11 each have a lower tip end 15 into which sampling fluids or reagents are drawn by the pipettor, and an upper mounting sleeve 16 into which a pipettor probe is inserted to attach the tip to the pipettor. The tips 11 shown in the drawings have mounting sleeves 16 that have approximately the same taper as the lower tip ends 15 and are provided with circumferentially spaced axially extending ribs 17. However, it should be noted that pipette tips are made in a variety of shapes, some of which have more cylindrical mounting sleeves, do not have ribs and/or are provided with a distinct separating shoulder between the mounting sleeve and the lower tip end. In the embodiment shown, the lower ends of the ribs 17 engage the upper face of the support surface 12 of the tip holder 10, however, such support function may be provided in alternate tip constructions by a separating shoulder or the like. In any event, in their support position on the tip holder 10, tips 11 are loosely supported for ready attachment to and withdrawal by the pipettor.

Figure 2:
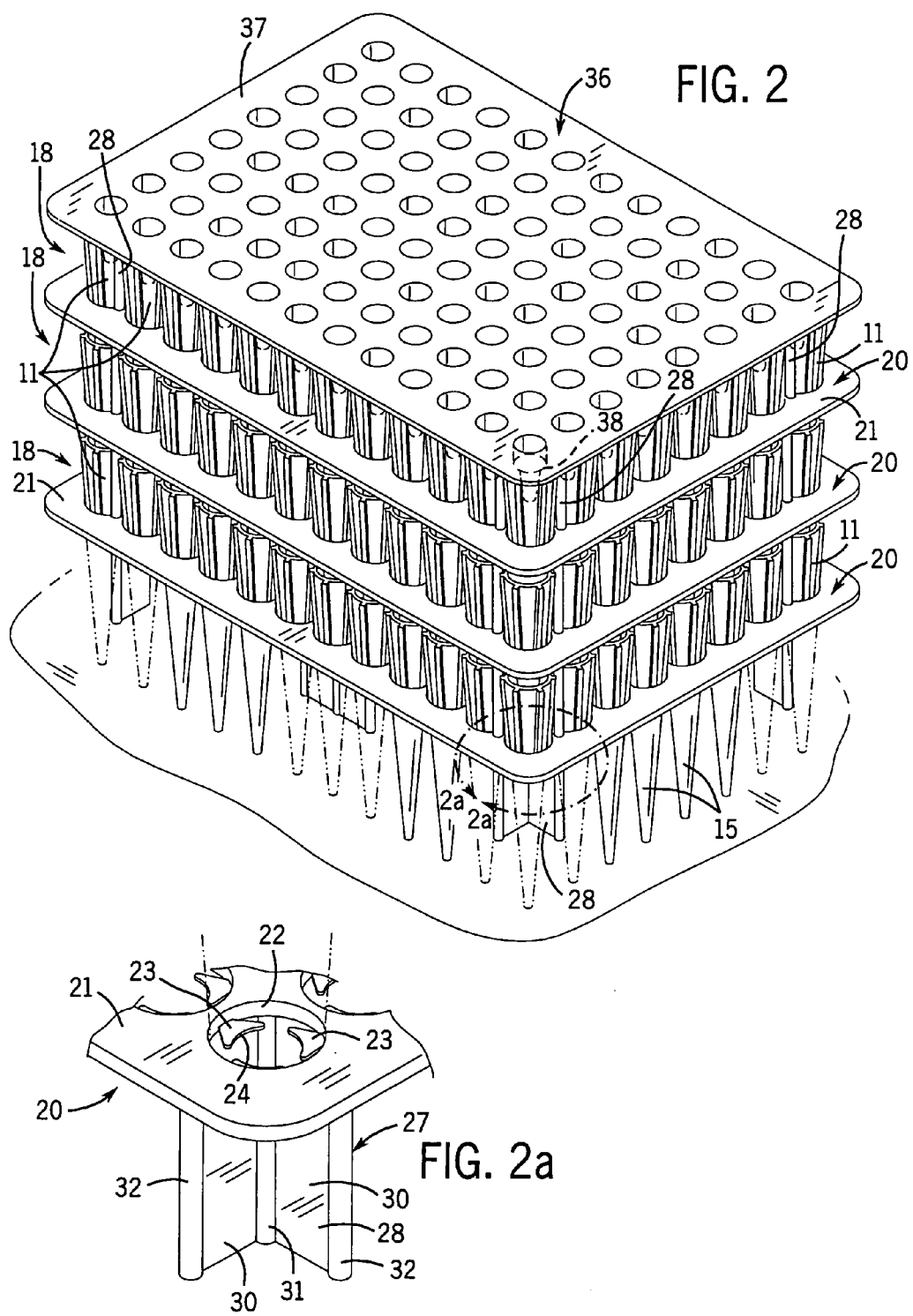
FIG. 2 is an isometric view of a tiered arrangement of trays of replacement pipette tips for use in the system and method of the present invention.

Referring also to FIG. 2, multiple arrays of tips 11 are shown stacked in tiers 18 with each tier of tips supported on a horizontal transfer plate 20. The transfer plate 20 includes a generally flat main body portion 21 that is provided with an array of apertures 22 in a pattern that corresponds to the openings 13 in the tip holder 10. The apertures 22 have a major diameter sufficient to permit a pipette tip 11 to easily pass therethrough. However, each aperture 22 is also provided with three circumferentially spaced flexible lips 23 that are formed integrally with the main body portion 21 and extend radially inwardly within the aperture. The lips 23 have radial inner edges 24 that lie on a common circular arc having a diameter approximately equal to diameters of the openings 13 in the main pipette tip holder. Thus, when a pipette tip is inserted by its lower tip end 15 through the aperture 22 in the transfer plate 20, the lower edges of the ribs 17 on the tip mounting sleeve define an interrupted shoulder 25 by which the tip is supported on the flexible lips 23. This arrangement is shown in detail in FIGS. 2a, 4 and 5. As best shown in FIGS. 2a and 5–8, the flexible lips 23 are substantially thinner than the flat main body portion 21 of the transfer plate 20. More particularly, the lips have a thickness less than half the thickness of the main body portion. The pipette tips 11 shown in the drawings have six circumferentially spaced and axially extending ribs 17 such that, regardless of the rotational orientation of a tip 11, there will always be a rib shoulder 25 in contact with and supported by a flexible lip 23.

In the tiered arrangement shown in FIG. 2, the lower tip ends 15 of each array of tips on a transfer plate 20 extend downwardly into the mounting sleeves 16 of the tips in the tier immediately below it. To maintain separation of the tiers (and to assist in reloading transfer of the tips as will be discussed hereinafter), each transfer plate 20 is provided with an integral downwardly depending support structure 26 on the underside of the main body portion 21. The support structure 26 comprises a plurality of legs 27 extending downwardly from and perpendicular to the underside of the main body portion 21. The legs 27 are of equal length, but are of slightly different horizontal cross sections depending on their location. For example, the corner legs 28 as shown in FIGS. 2, 2a and 3 have an angle or L-shaped cross section comprising two right angle webs 30 separated by a connecting rib 31 and having opposite edge beads 32. This construction provides the necessary rigidity for the transfer function to be described. Along the longer edge of the transfer plate 20, midway between the corner legs 28, is a supporting middle leg 33 which, in the preferred embodiment, comprises a T-section including a pair of outer webs 34 and an inwardly extending middle web (not shown). A center leg which is also not shown in the drawings preferably has an X-shaped cross section defined by four webs similar to webs 30 and 34, the center leg being directly aligned with the middle legs 33 on the opposite longer edges of the transfer plate. The corner legs 28 and middle legs 33 are also interconnected by stiffening webs 35, also extending downwardly from the underside of the main body portion 21 but being substantially shorter in length than the legs 27. The legs 26 and stiffening webs 35 provide a necessary rigidity to the transfer plate 20 required for the tip transfer function as will be described hereinafter.

In the reloading system of the present invention, the top tier 18 of tips 11, along with the transfer plate 20 in which they are supported, is picked up manually from the stack shown in FIG. 2. However, as is also shown in FIG. 2, a push plate 36 overlies the upper tier 18 of tips and the push plate is picked up along with the transfer plate 20 and tips supported therein and moved to a position above the support surface 12 of the tip holder 10, as shown in FIG. 3. The push plate 36 has a generally flat body 37 similar to the main body portion 21 of the transfer plate 20. An array of downwardly extending fingers 38 depend from the undersurface of the push plate body 37. The fingers are arranged to align with and extend into the mounting sleeves 16 of the tips 11 carried on the transfer plate 20. The fingers 38 have tapered distal ends 40 that are truncated to form a flat end. The opposite proximal end 41 of each finger, by which the finger is integrally joined to the undersurface of the push plate body, is cylindrical in shape. The cylindrical proximal end 41 has a diameter substantially greater than the maximum diameter of the distal end 40 so that at their juncture, there is a flat annular shoulder 42. The diameter of the shoulder 42 is approximately equal to the maximum diameter of the upper end of the mounting sleeve 16 of the tip 11. The diameter of the shoulder is also smaller than the major diameter of the apertures 22 in the transfer plate 20. Thus, when the push plate 36 is placed over the array of tips 11 in the transfer plate 20, tapered distal ends 40 of the push plate fingers 38 will enter the open upper ends of the tips and the shoulders 42 will rest on the upper edges of the mounting sleeves 16.

Figure 6:
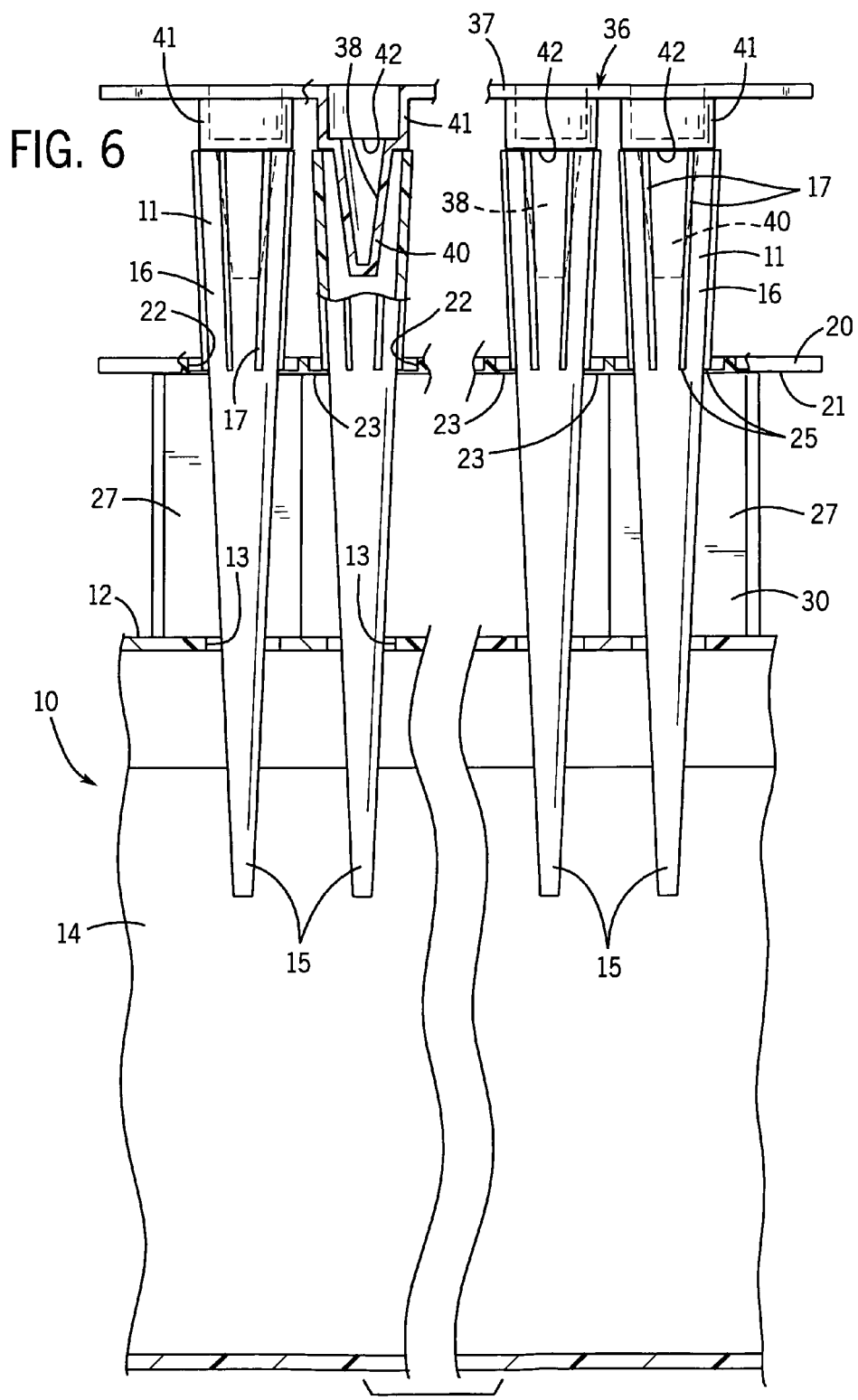
FIG. 6 is an enlarged vertical section taken on line 6—6 of FIG. 3, but showing the transfer tray, replacement tips and push plate moved into transfer position with respect to the tip holder.

To transfer the top tier 18 of pipette tips from the FIG. 2 positions to an empty tip holder 10, the entire subassembly shown in the upper portion of FIG. 3, comprising the transfer plate 20 loaded with tips 11 and on which rests the push plate 36, is simply lowered onto the support surface 12 of the tip holder with the lower tip ends 15 entering the openings 13 in the support surface. It has been found that, because the pipette tips are held loosely on the flexible lips 23 in the apertures in the transfer plate 20, they can be quite easily misaligned such that direct entry into the openings in the support surface of the tip holder might ordinarily be difficult. However, the presence of the upper push plate 36 with the fingers 38 extending into the pipette tips stabilizes the tips and maintains them in an accurately aligned array so the tips enter the openings in the tip holder readily and without the need for any manual intervention. As the pipette tip ends move into the holder, the bottom ends of the legs 27 on the transfer plate 20 come into supporting contact with the support surface 12 of the tip holder. This preliminary transfer position is shown in FIG. 6. The tips 10 remain suspended from the transfer plate 20 by engagement of the lower ends of the vertical ribs 17 on the tips with the flexible lips 23 in the transfer plate apertures 22. The transfer of tips is completed by unloading the transfer plate by pushing the tips through the transfer plate with the push plate 36 and allowing them to drop a short distance onto the support surface 12 of the tip holder where they are supported by engagement of the lower ends of the ribs 17 on the support surface edges surrounding the openings 13, as shown in FIG. 8.

The operation of the push plate 36 to effect the pipette tip transfer and reloading of the tip holder will now be described with reference to FIGS. 5–8. With the assembly in the FIG. 6 position, the upper push plate 36 is pressed downwardly in a uniform manner and, initially, the lower ends of the ribs 17 on the tips cause the flexible lips 23 which are supporting the tips to deflect downwardly and outwardly as shown by the arrows in FIG. 5. As downward movement of the push plate continues, the mounting sleeves 16 on the upper ends of the tips slide along the edges of the flexible lips 23 as a result of the bearing contact by the annular shoulders 42 of the push plate against the upper rims of the tips. Eventually, the shoulders 42 will engage the flexible lips and move past them, as shown in FIG. 7, whereupon the pipette tips are no longer supported by the flexible lips 23 and drop a short distance onto the support surface 12 of the tip holder where they are supported by engagement of the shouldered ends of the ribs 17 on the support surface 12, as shown in FIG. 8. The transfer plate 20 and push plate 36 lying on top of it are then lifted vertically away, leaving the tip holder reloaded with an array of tips in exactly the same way in which the tip holder was originally loaded. Importantly, there is no carrying plate, transfer plate or other structure interposed between the pipette tip ribs and the support surface 12 of the tip holder which would otherwise place the replacement tips at a slightly higher position on the holder than the original tips. As indicated above, the interposition of structure between the tip holder and the tips can interfere with the proper operation of mechanical or robotic pipettor systems.

Although the system and its method of operation have been described with respect to the transfer of pipette tips having a ribbed construction on the upper mounting sleeves 16, the system is equally useful with other pipette tip constructions utilizing, for example, tips in which the upper mounting sleeve defines a flat annular shoulder at its juncture with the lower tip end. All components of the system are made of plastic, but the transfer plate 20 uses far less plastic than a tip holder. For example, conventional tip holder 10 may weigh about 70 grams, whereas the transfer tray weighs only about 10 grams, thereby providing a reduction in plastic waste of about 85%. Also, the push plate can be reused with each of the tiered pipette tip arrays.

We claim:

1. A reloading system for transferring one of a plurality of tiers of pipette tip arrays from a vertically stacked orientation to an empty pipette tip holder, said system comprising:
    a pipette tip holder having a flat support surface provided with an array of tip support openings adapted to receive and hold an array of pipette tips;
    a plurality of stacked tiers of pipette tip arrays, wherein the pipette tips each have a lower tapered tip end, and an upper mounting sleeve separated from the tip end by a shoulder;
    a transfer plate in each tier holding a respective array of pipette tips, each transfer plate having a main body portion having an underside and a uniform thickness and an array of apertures arranged to align with the array of tip support openings in the pipette tip holder, each of the apertures having a peripheral edge portion including a plurality of flexible lips extending radially inwardly from the edges of the apertures, said lips adapted to support a pipette tip by its shoulder with the tip end extending downwardly through the aperture in the transfer plate;
    a support structure formed integrally with and depending downwardly from the underside of each transfer plate and engaged with the transfer plate of the tier immediately below in the stacked orientation to prevent supporting contact between vertically adjacent tips, said support structure operative to support the transfer plate on the flat support surface of the pipette tip holder; and,
    a push plate adapted to overlie each of the transfer plates individually and directly engage the mounting sleeves of the tips held in the array of apertures of the transfer plate and push the tips through the apertures, past and separated completely from the flexible lips and into the tip support openings on the pipette tip holder.

2. The system as set forth in claim 1 wherein said flexible lips are less than half the thickness of said main body portion.

3. The system as set forth in claim 1 wherein the underside of the main body portion of said transfer plate is flat and said flexible lips are coplanar with said flat underside.

4. The system as set forth in claim 1 comprising three flexible lips for each aperture, said lips positioned equally spaced around the aperture.

5. The system as set forth in claim 4 wherein the radially inner edges of the lips comprise circular arcs defining a diameter equal to the diameter of the openings in the pipette holder.

6. The system as set forth in claim 1 wherein said support structure comprises a plurality of legs extending perpendicular to the transfer plate and positioned between adjacent apertures.

7. The system as set forth in claim 1 wherein the push plate comprises an upper body having a planar undersurface and an array of fingers extending downwardly from the undersurface arranged to align with and extend into the mounting sleeves of the tips.

8. The system as set forth in claim 7 wherein each of said fingers comprises a tapered distal end sized to extend into the mounting sleeve of a tip, and a proximal end sized to pass through a transfer tray aperture and forming at a juncture with the distal end a shoulder adapted to engage the upper edge of the pipette tip mounting sleeve and push said upper edge past the flexible lips.

9. A method for transferring one of a plurality of tiers of pipette tip arrays from a vertically stacked orientation to an empty pipette tip holder, the pipette tips each having a lower tapered tip end and an upper mounting sleeve with a flat upper end and the pipette tip holder having a flat support surface provided with an array of tip support openings adapted to receive and loosely hold the array of tips, said method comprising the steps of:
    (1) providing an empty pipette tip holder having a flat support surface provided with an array of tip support openings adapted to receive and loosely hold an array of pipette tips;
    (2) providing a plurality of stacked tiers of pipette tip arrays, each tier of pipette tip arrays being held and supported by a transfer plate having a fiat body with an array of apertures arranged to align with the array of tip openings in the holder, wherein each of the apertures is formed with a flexible peripheral edge portion sized to support a pipette tip by its mounting sleeve with the tip end extending downwardly from an underside of the transfer plate body;
    (3) supporting all but the lowermost transfer plate on the adjacent transfer plate of the tier immediately below with a transfer plate support structure formed integrally with and depending downwardly from the underside of the respective transfer plate to prevent supporting contact between vertically adjacent tips in the stacked orientation;
    (4) positioning the transfer plate of the uppermost tier in the stack and the array of tips supported thereon over the empty pipette tip holder with the tip ends extending into the openings of the tip holder and the support structure resting on the support surface to prevent supporting contact of the tips by the tip holder;
    (5) providing a push plate having a plurality of downwardly depending protrusions corresponding to and alignable with the pipette tips held in the transfer plate, said protrusions including shoulders adapted to engage the upper ends of said upper mounting sleeves of the pipette tips;
    (6) aligning the push plate with the transfer plate positioned over the empty pipette tip holder and engaging the downwardly depending protrusions on the push plate with the mounting sleeves of the pipette tips in the transfer plate positioned over the empty pipette tip holder; and,
    (7) pushing the tips with the push plate protrusions through the apertures and causing the flexible edge portions to deflect downwardly until the upper ends of the tips and the shoulders are past the edge portions and the tips are free of the transfer plate to drop into the tip support openings on the pipette holder.

10. The method as set forth in claim 9 wherein the pipette tips are of the type wherein the tapered tip end and the upper mounting sleeve are separated by an intermediate shoulder and including the step of supporting the tips by their intermediate shoulders on the flexible peripheral edge portions of the apertures in the transfer plates.

11. The method as set forth in claim 9 comprising the step of forming said flexible edge portions with a thickness less than half the thickness of the flat body.

* * * * *